United States Patent [19]

Maurer et al.

[11] 4,256,892

[45] Mar. 17, 1981

[54] PREPARATION OF BIS-2-PYRIDYL-DISULFIDES

[75] Inventors: Manfred Maurer, Kirchheim; Winfried Orth, Hassloch; Werner Fickert, Mannheim, all of Fed. Rep. of Germany

[73] Assignee: Rutgerswerke Aktiengesellschaft, Frankfurt am Main, Fed. Rep. of Germany

[21] Appl. No.: 92,323

[22] Filed: Nov. 8, 1979

[30] Foreign Application Priority Data

Feb. 7, 1979 [DE] Fed. Rep. of Germany ....... 2904548

[51] Int. Cl.$^3$ ............................................ C07D 213/62
[52] U.S. Cl. .................................................. 546/261
[58] Field of Search ....................... 546/261; 260/608

[56] References Cited

U.S. PATENT DOCUMENTS

| 2,742,476 | 4/1956 | Bernstein et al. | 546/261 |
| 3,954,781 | 5/1976 | Hooks et al. | 546/261 |

*Primary Examiner*—Henry R. Jiles
*Assistant Examiner*—Robert T. Bond
*Attorney, Agent, or Firm*—Hammond & Littell, Weissenberger and Muserlian

[57] ABSTRACT

In a process for the preparation of bis-2-pyridyl-disulfide or bis-(2-pyridyl-1-oxide)-disulfide optionally substituted on the pyridyl ring with at least one substituent selected from the group consisting of halogen and alkyl and alkoxy of 1 to 4 carbon atoms by oxidation of the corresponding 2-mercapto-pyridine or its N-oxide, the improvement comprising effecting the oxidation in an aqueous acid media containing an alkali metal or alkaline earth metal chlorite.

8 Claims, No Drawings

PREPARATION OF BIS-2-PYRIDYL-DISULFIDES

STATE OF THE ART

Bis-2-pyridyl-disulfides, especially bis-(2-pyridyl-1-oxide)-disulfide, are widely used in commerce as antibacterials and fungicides in agriculture and in cosmetic preparations such as shampoos and for protecting synthetic textiles or fabrics against fungus attack as described in U.S. Pat. No. 2,742,476 and Canadian Pat. No. 501,851.

U.S. Pat. No. 2,742,476 describes the preparation of bis-2-pyridyl-disulfides by oxidation of 2-mercaptopyridines with hydrogen peroxide. As pointed out in DOS 2,519,715, the said oxidation has to be carried out over a relatively narrow pH throughout the entire reaction to obtain satisfactory yields as variations of only ±0.5 in the pH will result in 10 to 20% lower yields. Moreover, the use of peroxides involves handling risks and relatively costly safety measures.

DOS 2,617,489 describes replacing hydrogen peroxide with chloride or an alkali metal hypochlorite but this process also requires a pH range of 4 to 8 for economical yields and the pH value has to be constantly adjusted to neutralize the hydrochloric acid formed in the oxidation process.

OBJECTS OF THE INVENTION

It is an object of the invention to provide an improved economical process for the oxidation of 2-mercaptopyridines or their N-oxides in good yields and high purity.

This and other objects and advantages of the invention will become obvious from the following detailed description.

THE INVENTION

The novel process of the invention for the preparation of bis-2-pyridyl-disulfide or bis-(2-pyridyl-1-oxide)-disulfide optionally substituted on the pyridyl ring with at least one substituent selected from the group consisting of halogen and alkyl and alkoxy of 1 to 4 carbon atoms by oxidation of the corresponding 2-mercaptopyridine or its N-oxide, the improvement comprising effecting the oxidation in an aqueous acid media containing an alkali metal or alkaline earth metal chlorite.

Examples of the alkali metal and alkaline earth metal chlorites are sodium chlorite, potassium chlorite, lithium chlorite, calcium chlorite and magnesium chlorite. The chlorites may be added in solid form to an aqueous solution or suspension of the mercapto-pyridines or an alkali metal or alkaline earth metal salt thereof or in the form of an aqueous solution. Preferably, aqueous 24.2% sodium chlorite solution is used.

The pH of the reaction medium must be acid as there is no reaction in the alkaline range. The preferred pH range is 4.5 to 5.5, more preferably 4.0 to 5.0 and the reaction may be effected at temperatures from 0° to 70° C., preferably 20°-35° C. The pH may be adjusted by addition of a non-oxidizing mineral or organic acid such as hydrochloric acid or acetic acid.

The chlorite oxidizing agent may be added to the aqueous solution or suspension of the mercapto-pyridine which has been adjusted to the desired pH or the oxidizing agent may be added and the pH then adjusted. The oxidizing agent is preferably added in portions with agitation and is preferably used up to 20% stoichiometric excess with respect to the mercapto-pyridine to obtain maximum purity and yields. Preferably, the reaction mixture is stirred for 3 to 5 hours after addition of the chlorite to ensure completeness of the reaction.

The 2-mercapto-pyridines used as the starting materials are known compounds and may be prepared by reacting 2-chloropyridine or its N-oxide (see U.S. Pat. No. 2,951,844) with alkali metal sulfide or alkaline earth metal sulfide as described in U.S. Pat. Nos. 2,686,786 and 3,159,640.

The process has the advantage of producing the desired products in high yields and purity sufficient to meet purity requirements for further processing into cosmetic preparations without an additional purification step. Moreover, good results are obtained even when impure solutions of mercapto-pyridines are used, depending on the type of preparation.

Examples of suitable substituents on the pyridine ring are halogens such as bromine or chlorine and alkyl and alkoxy such as methyl, ethyl, isopropyl, propyl, butyl, methoxy, ethoxy, propoxy, isopropoxy and butoxy.

In the following examples there are described several preferred embodiments to illustrate the invention. However, it should be understood that the invention is not intended to be limited to the specific embodiments.

EXAMPLE 1

350 ml of water were added with stirring to 2000 ml (2440 g) of an aqueous sodium chloride solution containing 298 g (2 mole - 12.3%) of sodium 2-mercapto-pyridine -1-oxide and about 170 ml of concentrated hydrochloric acid were added thereto with stirring to obtain a pH of 4.5. The mixture was cooled to 20° C. and 68 g (0.6 mole) of solid 80% sodium chlorite were added portion wise with vigorous stirring over 60 minutes during which the temperature rose to 35° C. External cooling was used to keep the temperature between 20° and 35° C. and the mixture was stirred for 5 hours and was then vacuum filtered. The recovered solid was washed with 1000 ml of water and was dried at 100°-110° C. to obtain 219 g (87% yield) of bis-(2-pyridyl-1-oxide)-disulfide melting at 203°-205° C. Thin layer chromatography on silica gel plates F 254/366 with a 1—1 methanol-chloroform solvent and a 75-20-5 ethyl acetate-methanol-acetic acid mixture as the eluant was uniform.

EXAMPLE 2

The procedure of Example 1 was repeated using 224 g (0.6 mole) of a 24.2% aqueous sodium chlorite solution to obtain 232 g (92% yield) of bis-(2-pyridyl-1-oxide)-disulfide melting at 203°-205° C. and having a uniform thin layer chromatogram.

EXAMPLE 3

2920 g of an aqueous solution containing about 8% of sodium chloride, about 12% of sodium acetate and 10.2% (298 g-2 moles) of sodium 2-mercapto-pyridine-1-oxide was adjusted to a pH of 5 by addition of concentrated hydrochloric acid with vigorous stirring. 224 g of a 24.2% (0.6 mole) aqueous sodium chlorite solution were added dropwise with vigorous stirring over one hour at 20°-35° C. to the reaction mixture and the mixture was then stirred for 4 hours and was vacuum filtered. The recovered solid was washed with 1000 ml of water and dried at 100°-110° C. to obtain 230.5 g (91.8% yield) of bis-(2-pyridyl-1-oxide)-disulfide melting at 203°–205° C. and having a uniform thin-layer chromatogram.

EXAMPLES 4 to 8

Using the procedure of Example 2, the reaction with aqueous sodium chlorite was repeated at varying pH values and at different reaction temperatures and the results are reported in Table I.

TABLE I

| Example No. | pH value | Reaction Temp. °C. | % yield |
| --- | --- | --- | --- |
| 4 | 3.5 | 20–35 | 84.8 |
| 5 | 4.0 | 20–35 | 90.9 |
| 6 | 5.5 | 20–35 | 89.1 |
| 7 | 4.5 | 0–10 | 91.8 |
| 8 | 4.5 | 60–65 | 84.3 |

EXAMPLE 9

The procedure of Example 2 was repeated using acetic acid to adjust the pH to 5.5 to obtain 225 g (89.2% yield) of bis-(2-pyridyl-1-oxide)-disulfide melting at 203°–205° C. and having a uniform thin-layer chromatogram.

EXAMPLE 10

2440 g (2000 ml) of an aqueous sodium chloride solution containing 12.3% of sodium 2-mercapto-pyridine-1-oxide was mixed at 25° C. with 224 g (0.6 mole) of an aqueous 24.2% sodium chlorite solution and then 170 ml of concentrated hydrochloric acid were added thereto dropwise with stirring and external cooling to keep the temperature below 35° C. to obtain a pH of 4.5. The mixture was stirred for 5 hours and was vacuum filtered. The recovered solid was washed with 1000 ml of water and dried at 100°–110° C. to obtain 234 g (92.8% yield) of bis-(2-pyridyl-1-oxide)-disulfide melting at 203°–205° C. and having an uniform thin-layer chromatogram.

EXAMPLE 11

210 g (0.56 mole) of an aqueous 24.2% sodium chlorite solution were added dropwise at 25° C. over 15 to 30 minutes to a stirred mixture of 1500 ml of water, 222 g (2 moles) of 2-mercapto-pyridine, 50 ml of acetic acid and a few drops of a wetting agent and the mixture was stirred for 2 hours at room temperature and was then vacuum filtered. The recovered solid was washed with water and dried at 40° C. under a reduced pressure to obtain 202 g (92% yield) of 2,2'-bis-pyridyl-disulfide melting at 55°–56° C. and having an uniform thin-layer chromatogram.

Various modifications of the process of the invention may be made without departing from the spirit or scope thereof and it is to be understood that the invention is to be limited only as defined in the appended claims.

We claim:

1. In a process for the preparation of bis-2-pyridyl-disulfide or bis-(2-pyridyl-1-oxide)-disulfide optionally substituted on the pyridyl ring with at least one substituent selected from the group consisting of halogen and alkyl and alkoxy of 1 to 4 carbon atoms by oxidation of the corresponding 2-mercapto-pyridine or its N-oxide, the improvement comprising effecting the oxidation in an aqueous acid media containing an alkali metal or alkaline earth metal chlorite.

2. The process of claim 1 wherein the pH is 3.5 to 5.5.

3. The process of claim 1 wherein the pH is 4.0 to 5.0.

4. The process of claim 1 wherein the reaction temperature is 0° to 70° C.

5. The process of claim 1 wherein the reaction temperature is 20° to 35° C.

6. The process of claim 1 wherein the chlorite is used as an aqueous solution.

7. The process of claim 1 wherein the chlorite is used in a stoichiometric excess up to 20%.

8. The process of claim 1 wherein the chlorite is sodium chlorite.

* * * * *